United States Patent
Lackhart

(10) Patent No.: US 7,060,487 B2
(45) Date of Patent: Jun. 13, 2006

(54) ENCHANCED SENSITIVITY COUPLED FIBER-OPTIC BIOSENSOR CONFIGURATIONS

(75) Inventor: Michael D. Lackhart, Charlottesville, VA (US)

(73) Assignee: Veridian Systems Division, Charlottesville, VA (US)

( * ) Notice: Subject to any disclaimer, the term of this patent is extended or adjusted under 35 U.S.C. 154(b) by 664 days.

(21) Appl. No.: 10/093,347

(22) Filed: Mar. 7, 2002

(65) Prior Publication Data

US 2002/0127610 A1 Sep. 12, 2002

Related U.S. Application Data

(60) Provisional application No. 60/274,054, filed on Mar. 7, 2001, provisional application No. 60/274,280, filed on Mar. 8, 2001.

(51) Int. Cl.
*C12M 3/00* (2006.01)

(52) U.S. Cl. ............ 435/287.2; 356/448; 385/12; 385/30; 385/31; 385/39; 385/43; 385/123; 385/141; 422/57; 422/82.05; 422/82.11; 435/805; 436/527

(58) Field of Classification Search .......... 385/12, 385/30, 31, 39, 43, 123, 141; 356/448; 422/57, 422/82.05, 82.11, 287.2, 808, 527
See application file for complete search history.

(56) References Cited

U.S. PATENT DOCUMENTS

| 5,494,798 A | | 2/1996 | Gerdt et al. ............. 435/6 |
| 6,103,535 A | * | 8/2000 | Pilevar et al. ........... 436/518 |

* cited by examiner

*Primary Examiner*—Christopher L. Chin
(74) *Attorney, Agent, or Firm*—Gifford, Krass, Groh, Sprinkle, Anderson & Citkowski, PC

(57) ABSTRACT

Coupled fiber-optic, evanescent-wave biosensors are improved through the use of configurations which adjust certain optical characteristics for enhanced sensitivity. In the preferred embodiment, this is carried out by inputting light into the coupler at either a different wavelength or multiple wavelengths simultaneously. In alternative embodiments, different modulation schemes and/or interferometric schemes are utilized. For example, at each of the inputs, different carrier frequencies may be used and modulated at lower frequencies, including prime-number frequencies. As the refractive index is changed in the vicinity of the coupling, a shift in the wavelength will induce a phase shift in the baseline signal such that, during data collection, the sensor is able to detect more refined changes. In general, through appropriate choice of input wavelength, fewer operational points will fall in an inefficient local maximum or minimum, thereby affording much greater sensitivity. The output(s) of the coupler are monitored in terms of frequency, with specific attention being paid in terms of a guard band on either side of a center frequency of interest. Multiple wavelength input may be introduced in a variety of ways, including switching between wavelengths, or through appropriate filtering, pulse-, phase- or amplitude modulation, and combinations thereof.

7 Claims, 4 Drawing Sheets

ENCHANCED SENSITIVITY COUPLED FIBER-OPTIC BIOSENSOR CONFIGURATIONS

REFERENCE TO RELATED APPLICATION

This application claims priority from U.S. provisional patent application Ser. Nos. 60/274,054, filed Mar. 7, 2001; and 60/274,280, filed Mar. 8, 2001, the entire contents of both of which are incorporated herein by reference.

FIELD OF THE INVENTION

This invention relates generally to fiber-optic, evanescent-wave biosensors and, in particular, to sensors wherein one or more optical attributes are altered to enhance sensitivity.

BACKGROUND OF THE INVENTION

Optical fibers are being used in a variety of sensor applications. For example, as discussed in U.S. Pat. No. 5,494,798, a pair of optical fibers may be pulled into a fused biconical coupler and used without cladding to exploit the evanescent field present immediately outside the fiber coupler waist/air interface. If an antibody is attached to the exposed surface of the bare fiber, the evanescent field envelopes the molecule.

When an antigen subsequently attaches to the antibody, there are changes in the evanescent field can force a shift in the output coupling ratio. This results in an optically detectable characteristic signal.

Whereas previous fiber-optic evanescent-wave sensors utilized multi-mode fibers, the '798 patent improved on the technique by employing a pair of single-mode optical fibers in a coupler arrangement. Light is introduced into one of the fibers to produce an evanescent region surrounding the coupling area, and the magnitude of light emitted from the pair of fibers is compared for detection purposes.

FIG. 1, taken from the '798 patent, shows the overall fiber optic system generally at 10. Light from laser diode 14 is inserted into a first leg 17 of a fiber optic coupler 18, and exits on the same fiber at 19 (input channel). A second fiber 20 provides an output channel for light from the first leg 17. A first photo diode detector 21 is connected to the input channel and a second photo diode detector 22 is connected to the output channel.

Each detector feeds its own transimpedance amplifier. The outputs of the transimpedance amplifiers 23, 24 are applied to A/D converters 25 and 26 which provide digital electrical signals along wires 27 and 28 to an instrumentation board 29. The instrumentation board 29 is then connected to a personal computer 30 which provides outputs to a printer or a monitor.

The finished probe includes the coupler and attached antibodies, which yields a baseline ratio for the sensor. The finished probe is then exposed to a material of interest, and the ratio of the light through the two sides of the coupler changes as a function of the way in which the target attaches. That is, the localized index of refraction at the coupling region and the determination of the ratio is a function of the binding in the coupler region.

In terms of the coupler itself, existing designs use off-the-shelf components intended for multiplexers and demultiplexers in telecommunications applications. Coming, for instance, makes these couplers by twisting together two or more 1300-nm, single-mode SMF 9–125 optical fibers, heating up the twisted area and pulling the ends apart to create a necked-down, nearly fused union. The number of fibers and other factors such as the proportion of each fiber in the twisted region determines the coupling ratio.

SUMMARY OF THE INVENTION

This invention improves upon the art of coupled fiber-optic, evanescent-wave biosensors through the use of configurations wherein one or more optical attributes are altered for enhanced sensitivity.

In one preferred embodiment, this is carried out by inputting light into the coupler at either a different wavelength or multiple wavelengths simultaneously. For example, at each of the inputs, different carrier frequencies may be used and modulated at lower frequencies, including prime-number frequencies.

The wavelength through the coupler is shifted by the change in index based upon the bound material. As the refractive index is changed in the vicinity of the coupling, a shift in the wavelength will induce a phase shift in the baseline signal such that, during data collection, the sensor is able to detect more refined changes. In general, through appropriate choice of input wavelength, only one of operational points will fall in an inefficient local maximum or minimum, whereas the other two will fall on a slope, thereby affording much greater sensitivity.

The output(s) of the coupler are monitored in terms of frequency, with specific attention being paid in terms of a guard band on either side of a center frequency of interest. Multiple wavelength input may be introduced in a variety of ways, including switching between wavelengths, or through appropriate filtering, pulse-, phase- or amplitude modulation, and combinations thereof.

DETAILED DESCRIPTION OF THE INVENTION

Although the basic concept of a fiber-optic coupler as presented in U.S. Pat. No. 5,494,798 is useful in the detection of certain biologic substances, the approach could be made more sensitive by adjusting certain attributes of the light input to, or output from, the coupler to improve detection sensitivity. Broadly, these adjustments include various modulation schemes inducing changes in wavelength, phase, and other characteristics.

Figure 1:
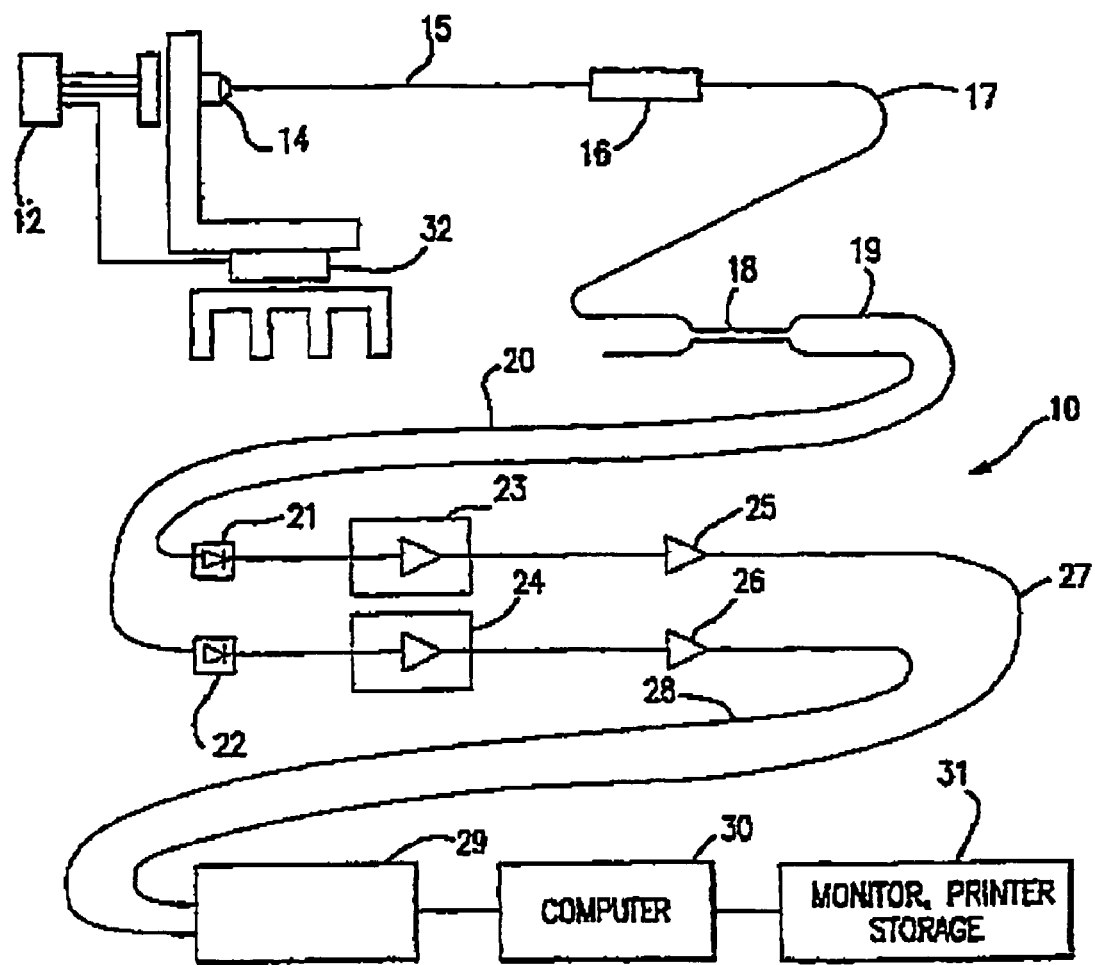
FIG. 1 is a diagram that depicts a prior-art coupled optical-fiber evanescent-wave biosensor.
Figure 2:
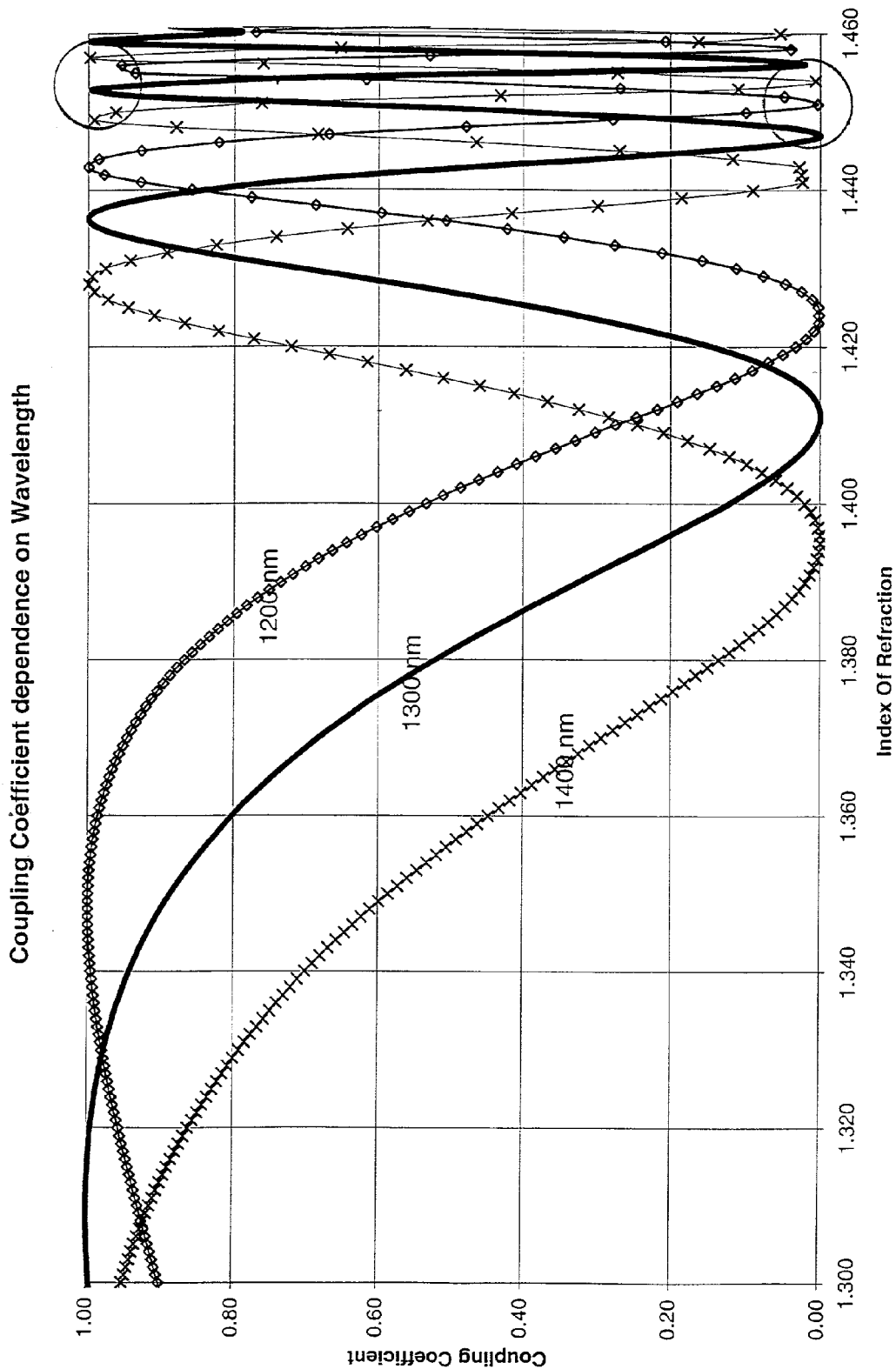
FIG. 2 is a graph which shows how index of refraction changes as a function of the output coupling ratio when the coupling region is immersed in solution and the binding partners attach.

With respect to varying the wavelength of the light input to the coupler so as to enhance resolution, FIG. 2 is a graph which shows how index of refraction changes as a function of the output coupling ratio when the coupling region is immersed in solution and the antibodies attach. Note that the system is most efficient when the baseline ratio is on the steep portion of a curve as opposed to a local maximum or minimum. That is, operation in the circled areas is limiting because a substantial change in the index results in relatively little change in the ratio. By operating on the steep initial slope of the curve, a very small change in refractive index which would occur during the binding of a low level of antigens will cause a significant shift in ratio which is more readily detected. Note also that the higher the numerical index, the steeper the slopes tend to be.

In FIG. 2, the solid curve is representative of ratio as a function of the change in index of refraction versus coupling ratio with light input at a wavelength of 1300 nanometers. The output coupling ratio is governed by many variables. A major variable being the wavelength of the light in the fiber. Different wavelengths will have different output coupling ratios. It happens if the wavelength is changed, to 1400 nm, for example, the curve is somewhat 'lagged.' Conversely, at a wavelength of, say, 1200 nm, the curve is a bit leading.

The optical detector is actually the combination of the necked-down coupler in combination with a biomolecular coating of some kind. If it happens that, based on the chemistry of the system, that operation is occurring in one of the circled regions, more optimum conditions may be achieved by adjusting the wavelength. In practice, this may be carried out by inputting light into the coupler at either a different wavelength or multiple wavelengths simultaneously. Multiple wavelength input may be accomplished in a variety of ways, including switching between wavelengths, or through appropriate filtering, pulse, phase or amplitude modulation, and combinations thereof. Extension to these other methodologies would be apparent to one of skill in the art of optoelectronics.

Figure 3:
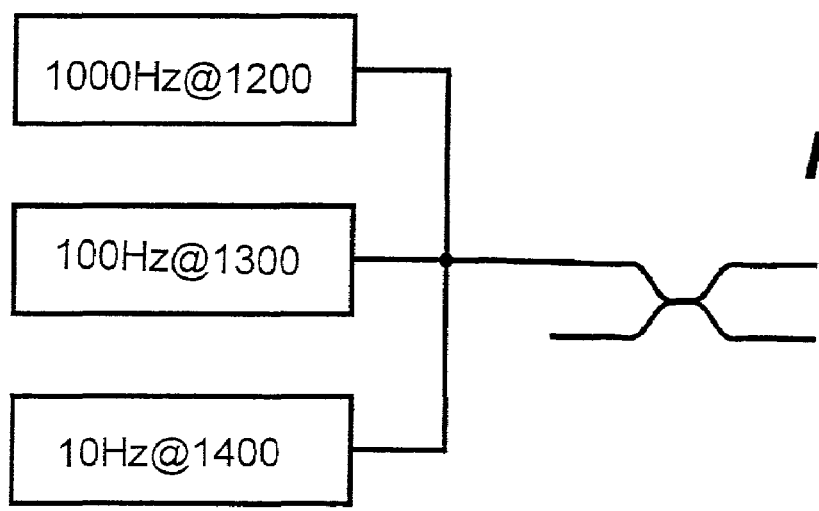
FIG. 3 is a simplified block diagram which illustrates the use of wavelength multiplexing to realize a multiple-wavelength input configuration according to the invention.
Figure 4:
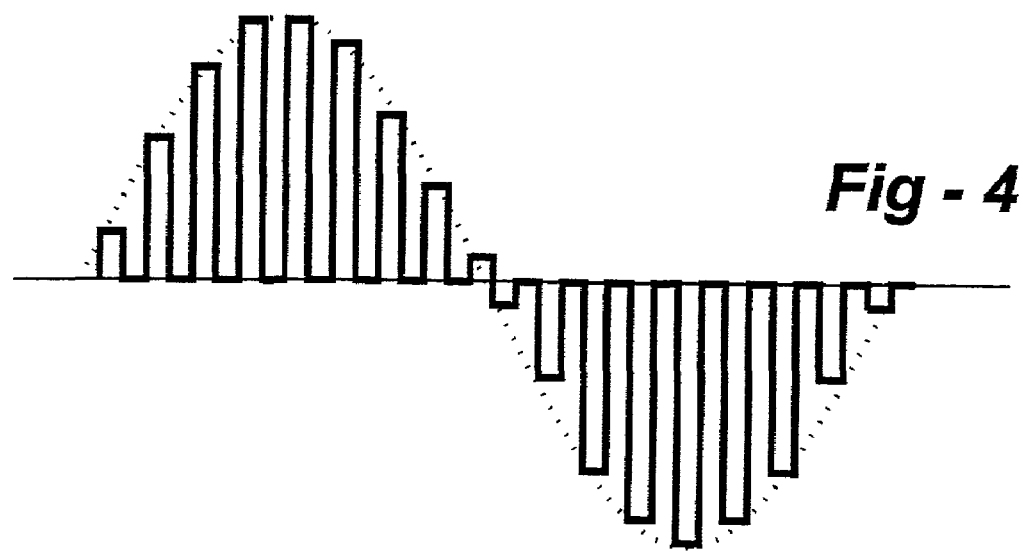
FIG. 4 is a curve which shows how different carrier frequencies may be used and modulated at lower frequencies.

FIG. 3 is a simplified block diagram which illustrates the use of wavelength multiplexing to realize a multiple-wavelength input configuration according to the invention. On the inputs, different carrier frequencies may be used and modulated at lower frequencies, as depicted in FIG. 4. For example, the carrier signals may be at 1200, 1300, and 1400 nm, and modulated at prime number frequencies. The prime signals would act as carriers for the coupling ratio and would be easily separated at the output.

Since the wavelength through the coupler is shifted by the change in index based upon the bound material, it follows that if the refractive index is changed in the vicinity of the coupling, a shift in the wavelength will induce a phase shift in the baseline signal. The result of this baseline manipulation is that during data collection the sensor is always capable of making the most sensitive measurement, that measurement that occurs alone the slope of the coupling curve not at the maxima or minima.

The output(s) of the coupler are monitored in terms of frequency, with specific attention being paid in terms of a guard band on either side of a center frequency of interest. In general, through appropriate choice of input wavelength, only one of operational points will fall in an inefficient local maximum or minimum, whereas the other two will fall on a slope, thereby affording much greater sensitivity.

Interferometric Embodiment

Figure 5:
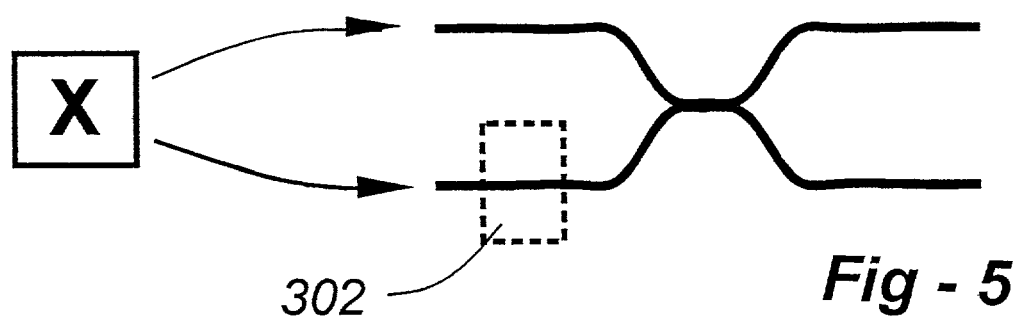
FIG. 5 is a simplified diagram that illustrates the use of a single coupler and phase shifter according to the invention.

According to a different embodiment of the invention, interferometry techniques and phase modulation of the coupling region are used to enhance detection sensitivity. The well-known Mach-Zenhnder interferometer will be used as an example, with the understanding that other configurations will be apparent to those of skill in the art. Broadly according to the invention, light having a nominal wavelength X is injected into both inputs of the optical coupler, but where a phase shifter 302 is used in at least one of the paths to introduce a slight shift in the nominal wavelength, as shown in FIG. 5. Any appropriate type of shifter may be used, including adjustments in fiber length, piezoelectric, and so forth.

Given two signals with one being phase-shifted relative to the other a waveform of constructive vs. destructive interference will be realized in accordance with the phase shift. A primary object of the invention is to utilize the phase-shifting to operate on a fringe between constructive and destructive interference such that the slightest change in the index of refraction will cause an almost digital transformation between constructive and destructive interference.

In practice, with the antibody in solution attached to the coupler, the phase of the nominal wavelength would be shifted back and forth while the target is introduced. When a dramatic shift in output is experienced due to the effect of the interference, the phase shift would be locked in place for subsequent detection purposes. Note that although a single coupler and phase shifter is depicted in FIG. 5, other arrangements are possible, including comparisons of one coupler against a reference coupler, for example. Fiber optic couplers have been used to make interferometric sensors, where the sensing is performed on one of the arms of the coupler. This technology makes the coupler the sensing region, significantly enhancing sensitivity.

Modulation Embodiment

According to a different embodiment of the invention, carrier signal modulation schemes are used to increase signal to noise ratio thereby improving sensitivity and reproducibility. Different types of carrier modulations produce different effects. These modulation applications would allow for enhanced signal analysis utilizing Digital Signal Processing technologies. A significant enhancement of distinguishing between signal and noise. Laser/source chopping or input modulation, output or Q-switch modulation and surface acoustic wave (SAW) devices may be used in conjunction with the optical coupler arrangement.

Figure 6:
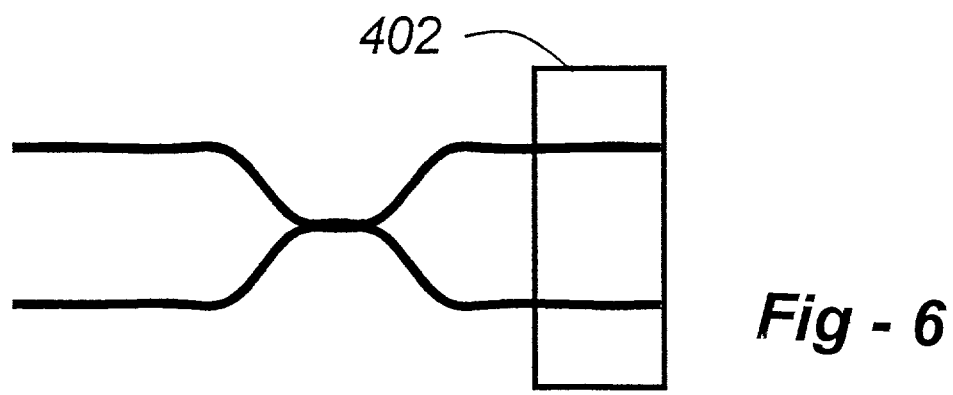
FIG. 6 is simplified drawing used to show how a piezoelectric transducer attached to a quarter-wave plate may be used to enhance signal transduction.

In FIG. 6, a piezoelectric transducer 402 is attached to a quarter-wave plate, which is physically coupled to both fibers of the sensor. By applying an acoustic signal at 1300 gigahertz, the acoustic transducer may be used to beat against the primary signal by relatively small amount setting up the opportunity to develop systematic surges (Brillion Scattering) which can be used to enhance signal transduction.

In general, the "activity of interest" will be long compared to the frequency of the carrier modulation, a signal modulated in such a manner will yield an improved signal-to-noise ratio. This approach may take advantage of a lock-in amplification or other ASP/DSP analysis. FFT and other waveform frequency analysis algorithms can be utilized. Commercial devices of this kind are relatively inexpensive, even up to frequencies of 100 gigahertz or more.

APPLICATIONS

This invention provides a sensitive detector having a wide variety of applications in the fields of biology, biochemistry and chemistry, and in many clinical applications. Although the terms "antigen" and "antibody" are used herein, it will be appreciated that is a special case, and that the invention finds utility beyond the more general target-specific molecular recognition. Indeed, the invention is applicable to both direct types of lock-and-key molecular recognition and indirect mechanisms, for example, subclasses of carbohydrates that are based upon more of a pattern match than a precise attachment mechanism.

In broad and general terms, the invention sense a change in one or more optical properties due to chemical/biochemical/bioaffinity/immunogenic-type interactions of biomolecules (ligands) with their respective binding partners. The terms ligand and its binding partner for the ligand or, simply, binder will be used to represent the two components in specific bioaffinity binding pairs, all of which are capable of recognizing and binding with the other partner in a bimolecular recognition pair. References to "biomolecular" or "molecular constituent," "binding partner," and so forth are used interchangeably and are not intended to in any way limit the invention, since the invention is applicable to any type of organic/inorganic material, so long as the interaction of one component causes a change in any optical property detectable by the apparatus. Interactions to which the invention is applicable include, but are not limited to, antigen-antibody, carbohydrate-lectin, receptor-ligand, binding protein-toxin, substrate-enzyme, effector-enzyme, inhibitor-enzyme, complimentary nucleic acid strands, binding protein-vitamin, binding protein-nucleic acid, reactive dye-protein, and reactive dye-nucleic acid interactions.

A molecular constituent useful in the present invention is characterized by an ability to specifically interact with another molecule, the interaction resulting in a change in an optically detectable property. A molecular constituent is any molecule, or portion of a molecule, that is capable of being attached, directly or indirectly to a waveguide such that it is capable of specific interaction with another molecule present in a test sample. Examples of a molecular constituent illustratively include a protein, a peptide, a polysaccharide, a sugar, an antibody, an antigen, a hapten, a receptor, a ligand such as an agonist or antagonist, a sugar binding protein such as a lectin, a toxin, a virus, a bacterium, a cell, a cell component such as an organelle, a particle such as a liposome, a nucleic acid, a drug and a prion. A molecular constituent further includes fragments or metabolites of the listed substances capable of specific interaction as described. Further, a molecule interacting with another molecule of the present invention is a gas illustratively including NO, $O_2$, $CO_2$. A molecular constituent also illustratively includes a chemical-sensitive polymer, a chemical-sensitive microimprinted polymer and a chemical-sensitive dye.

The terms "interaction" and "binding" are used interchangeably herein and refer to a selective association, through chemical or physical means, of two or more molecules. By "selective association" is meant that a first molecule binds preferentially to a second molecule or with greater affinity than to most other molecules. For example, a DNA molecule will selectively associate with a substantially complementary sequence and not with unrelated nucleic acids.

A test sample containing a molecular constituent to be detected is typically a biological sample. A biological sample is obtained from a human or other animal or from an environmental site where the earth, water or air are to be tested. Environmental sites include outdoor locations as well as indoor location such as laboratories, hospitals and manufacturing facilities. A sample illustratively refers to a cells, tissue or physiological fluid, such as plasma, serum, cerebrospinal fluid, saliva, semen, amniotic fluid, tears, milk, and fluids obtained from respiratory, upper digestive, intestinal, and genitourinary tracts. A test sample also includes fluid or a suspension of solids obtained from wounds, tumors and organs. Further, a test sample is obtained to test for environmental contamination. For example, a surface suspected to be contaminated by bacteria is swabbed and the bacteria obtained are suspended in a solution for later introduction into a biosensor of the present invention.

In one embodiment of the present invention, the interaction of molecular constituents acts to cleave or release molecules attached to the waveguide. For example, a substrate is attached to a waveguide and an enzyme to be detected interacts with the substrate under appropriate conditions. The resulting enzyme activity cleaves the substrate causing a change in an optical property.

In an embodiment of the instant invention, the interaction of molecular constituents results in the formation of another molecular species such that a change in an optical property is detected. For example, an enzyme interacts with a substrate to produce a product deposited on or near the waveguide such that a change in an optical property is detected. Techniques of enzymatic reaction are well known in the art. A preferred example is horseradish peroxidase used in conjunction with diaminobenzidine and $H_2O_2$ or a similar substrate such as tetramethylbenzidine or aminoethylcarbazole.

The term "attached" as used herein to describe the relationship of a first molecular constituent with a waveguide is intended to mean attached either directly or indirectly to the waveguide. An illustrative example of a direct attachment is a link to a pendant moiety on a waveguide via a pendant chemical moiety present on the first molecular constituent. An indirect attachment occurs, for example, where a molecular constituent is optionally attached to a waveguide via a linker. Where a linker is used the choice of linker depends on the surface of the waveguide and the molecular constituent to be attached. Selection of an appropriate combination will be evident to one skilled in the art. For example, where the surface has available Si-OH groups, appropriate linkers include aminoalkyltrialkoxysilanes, aminoalkyltrichlorosilanes, carboxyalkyltrialkoxysilanes, epoxyalkyltrialkoxysilanes, hydroxyalkyltrialkoxysilanes and hydroxyalkyltrichlorosilanes. Further suitable silanes are listed in Silicon Compounds: Register & Review, from United Chemical Technologies, 5th Ed., 1991. Further illustrative examples of linkers include aryl acetylene, diamines, diacids, polyalcohols, polyesters, polyethers, polylysine, polyarginine, polystyrene sulfonate, dextran sulfate, chondroitin, polyacrylic acid, polymethacrylic acid, polyacrylamide, polyallylamine, maleic acid, substituted or unsubstituted polyalkylenes, polyamines, polyamides, polysufonates, polyoxides, polyalkyleneglycols, polystyrenic-based polymers, polyacetals, polysaccharides, polycarbonates, polyurethanes, polyureas, polyamides, polyethyleneimines, polyarylene sulfides, polysiloxanes, polyimides, polyacetates, polymers of monoethylenically unsaturated monomers, polymers of polyvinylidene monomers and mixtures and copolymers of the above polymers. Following linker binding, unreacted functional groups on the waveguide surface are optionally blocked to prevent further reaction.

It will be appreciated by one skilled in the art that a molecular constituent attached to a waveguide is removable according to the mechanism of attachment used. Thus, a wave guide according to the invention is reusable.

An apparatus of the present invention allows detection of a molecular constituent in a test sample where the concentration of the constituent is in the range of $10^{-3}$ M to $10^{-15}$ M or less. Sensitivity of the apparatus will depend in part on the amount and concentration of the constituent attached to the waveguide.

Substances are optionally introduced into the cavity 140 to facilitate an interaction between molecular constituents. For example, a gel is introduced into the cavity. Gels operative in the present invention are any that do not interfere with the desired interaction and illustratively include agarose and acrylamide. The viscosity of a gel is chosen such that a molecular constituent in a sample to be tested remains in the cavity available for interaction with the waveguide attached molecular constituent for an appropriate period of time which is apparent to one of skill in the art.

It will be readily apparent to one of skill in the art that specific interaction between molecular constituents is to some extent dependent on appropriate interaction conditions such as temperature, salt concentration and buffer composition. Solutions used in a biosensor apparatus of the present invention are adjusted according to the desired interaction. An apparatus of the present invention optionally has a thermostatic control for regulating the temperature at which the molecular constituents are brought into contact.

The interaction of molecular constituents causing a change in an optical property is not limited to the interaction of two constituents. Thus, interaction of three or more molecules may be required to cause an optical change. For example, an antibody attached to a waveguide interacts with an antigen to be detected resulting in minimal or undetectable change in an optical property. A third molecular constituent, such as an antibody interacts with the antigen-antibody complex to bring about a change in an optical property.

As a final note, although the invention assumes the use of glass fibers, polymeric fibers and other materials may be used, depending upon the wavelengths of interest or other aspects of the particular analytical configuration. Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

I claim:

1. An enhanced sensitivity optical biosensor, comprising:
    a fiber-optic coupler having a refractive index incorporating at least two optical fibers, each fiber having an input and an output;
    a source of light having a nominal wavelength coupled to at least one of the inputs;
    the coupler including a necked-down section around which an evanescent field is generated when the light passes through;
    a biomolecule enveloped by the evanescent field, the biomolecule exhibiting a direct or indirect affinity to a binding partner, such that attachment of the binding partner causes a change in the refractive index of the coupler which, in turn, causes a change in the ratio of the light at the fiber outputs;
    apparatus separate from the source of light for adjusting the nominal wavelength of the light source so that a given change in the refractive index of the coupler causes a greater change in the ratio of light present at the fiber outputs; and
    instrumentation for receiving die light from the fiber outputs and for determining a characteristic of the binding partner in accordance with the change in the ratio of the light at the fiber outputs.

2. The optical biosensor of claim 1, wherein the biomolecule and binding partner include one or more of the following:
    antigen-antibody,
    substrate-enzyme,
    effector-enzyme,
    inhibitor-enzyme,
    complimentary nucleic acid strands,
    binding protein-vitamin,
    binding protein-nucleic acid,
    reactive dye-protein, and
    reactive dye-nucleic acid interactions.

3. The biosensor of claim 1, wherein the apparatus is a modulator for altering the nominal wavelength of the light source.

4. The biosensor of claim 3, wherein the modulator is a pulse-, phase-, carrier- or amplitude modulator.

5. The biosensor of claim 1, wherein the apparatus further includes a device for switching between wavelengths to alter the nominal wavelength of the light source.

6. The biosensor of claim 1, wherein the apparatus further includes a device for filtering the input to alter the nominal wavelength of the light source.

7. The biosensor of claim 1, wherein multiple different wavelengths are delivered to the coupler simultaneously.

* * * * *

UNITED STATES PATENT AND TRADEMARK OFFICE
CERTIFICATE OF CORRECTION

PATENT NO. : 7,060,487 B2  Page 1 of 1
APPLICATION NO. : 10/093347
DATED : June 13, 2006
INVENTOR(S) : Michael D. Lockhart It is certified that error appears in the above-identified patent and that said Letters Patent is hereby corrected as shown below:

Title Page
Item 12, Replace "Lackhart" with --Lockhart--.

Item 75, Replace "Lackhart" with --Lockhart--.

Column 1, line 64, Replace "Coming," with --Corning,--.

Signed and Sealed this

Nineteenth Day of December, 2006

JON W. DUDAS
*Director of the United States Patent and Trademark Office*